United States Patent [19]

Richardson

[11] 4,404,216
[45] Sep. 13, 1983

[54] ANTIFUNGAL 1,3-BIS-TRIAZOLYL-2-PROPANOL DERIVATIVE

[75] Inventor: Kenneth Richardson, Canterbury, England

[73] Assignee: Pfizer Inc., New York, N.Y.

[21] Appl. No.: 383,866

[22] Filed: Jun. 1, 1982

[30] Foreign Application Priority Data

Jun. 6, 1981 [GB] United Kingdom ................. 8117379
Oct. 17, 1981 [GB] United Kingdom ................. 8131370
Mar. 4, 1982 [GB] United Kingdom ................. 8206329

[51] Int. Cl.$^3$ ..................... A01N 43/64; A61K 31/41; C07D 249/08
[52] U.S. Cl. ............................. 424/269; 260/665 R; 260/665 G; 548/262; 549/563; 568/335; 568/812

[58] Field of Search ......................... 548/262; 424/269

[56] References Cited

FOREIGN PATENT DOCUMENTS 44605 1/1982 European Pat. Off ............. 548/262
2078719 1/1982 United Kingdom ................ 548/262

Primary Examiner—Alton D. Rollins
Attorney, Agent, or Firm—Charles J. Knuth; Peter C. Richardson

[57] ABSTRACT 2-(2,4-Difluorophenyl)-1,3-bis(1H-1,2,4-triazol-1-yl)propan-2-ol and its pharmaceutically acceptable acid addition salts are disclosed. This particular bis-triazole derivative and its aforesaid salts are useful for treating fungal infections in animals, including humans. Methods for preparing these compounds from known starting materials are provided.

3 Claims, No Drawings

ANTIFUNGAL 1,3-BIS-TRIAZOLYL-2-PROPANOL DERIVATIVE

BACKGROUND OF THE INVENTION

This invention relates to a novel bis-triazole derivative, which has antifungal activity and is useful in the treatment of fungal infections in animals, including humans.

British patent application No. 2,078,719A, published Jan. 13, 1982 and European patent application No. 44,605, published Jan. 27, 1982 (both assigned to Imperial Chemical Industries Limited) disclose compounds of the general formula:

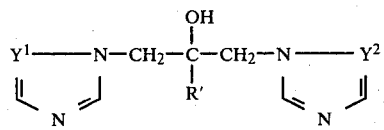

where $R^1$ is an optionally-substituted alkyl, cycloalkyl (e.g., cyclopentyl or cyclohexyl), aryl (e.g., phenyl or 2,4-dichlorophenyl) or aralkyl (e.g., benzyl) group, and $Y^1$ and $Y^2$ are =CH— or =N—; and salts or metal complexes and ethers or esters thereof. These compounds are stated to be useful as fungicides and as plant growth regulants. They are also stated to be active against the fungus diseases of humans. Among the compounds specifically disclosed therein are such bis-triazole derivatives as 2-(2,4-dichlorophenyl)-1,3-bis(1H-1,2,4-triazol-1-yl)propan-2-ol and its corresponding 2- and 4-chlorophenyl analogs. The corresponding 3-chlorophenyl and 4-bromophenyl compounds are also embraced by the statement of invention. However, these particular compounds have now been found to be teratogenic, which severely limits their use in treating human mycoses.

SUMMARY OF THE INVENTION

According to the present invention, there is now provided for the first time an antifungal compound of the formula:

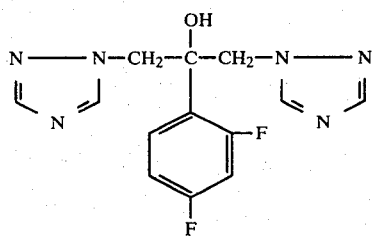

including the pharmaceutically acceptable salts thereof. This particular compound is not specifically disclosed in both the aforementioned Imperial Chemical Industries (I.C.I.) Limited applications, nor is the 2,4-difluorophenyl moiety specifically named as a preferred example of the "$R^1$" group in their general structural formula. Moreover, this particular compound, viz., 2-(2,4-difluorophenyl)-1,3-bis(1H-1,2,4-triazol-1-yl)propan-2-ol, is not teratogenic and thereby avoids the major disadvantage associated with the aforesaid I.C.I. compounds (where $R^1$ is other than 2,4-difluorophenyl).

Accordingly, the present invention specifically comprises an antifungal compound selected from the group consisting of 2-(2,4-difluorophenyl)-1,3-bis(1H-1,2,4-triazol-1-yl)propan-2-ol [the compound of the formula (I)] and the pharmaceutically acceptable acid addition salts thereof.

The invention also provides a pharmaceutical composition comprising a compound of the formula (I), or a pharmaceutically acceptable acid salt thereof, together with a pharmaceutically acceptable carrier or diluent. The composition is preferably for human use and is normally in capsule, tablet, injectable or ointment form.

In addition, the invention further provides a method of treating a fungal infection in an animal, including a human being, which comprises administering to said infected animal an effective antifungal amount of a compound of the formula (I), or a pharmaceutically acceptable acid addition salt thereof, or a pharmaceutical composition comprising such a compound or salt together with a pharmaceutically acceptable carrier or diluent.

DETAILED DESCRIPTION OF THE INVENTION

The compound of the formula (I) can be obtained by a number of different processes. In one process (1) according to the invention, it is obtained by reacting the oxirane compound of the formula:

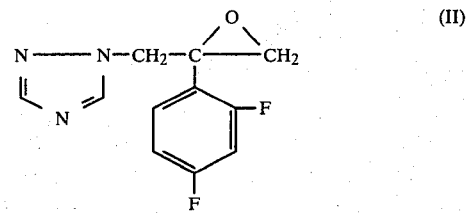

with 1,2,4-triazole, preferably in the presence of a base. The preferred bases in this connection are potassium carbonate and sodium hydride. When the triazole starting material is employed in the form of an acid addition salt, like the mesylate salt, an excess of base should be used.

In a typical procedure, the oxirane compound (II) and 1,2,4-triazole are reacted together in the presence of anhydrous potassium carbonate in a suitable organic solvent, such as dry dimethylformamide, preferably with heating to a temperature of ca. 50°–120° C. in order to accelerate the reaction, which is generally complete within a period of eight hours or less. The bis-triazole final product (I) can then be isolated and purified by conventional means.

The oxirane starting material of formula (II) can also be obtained by conventional means and this is accomplished by reacting the corresponding ketone of the formula:

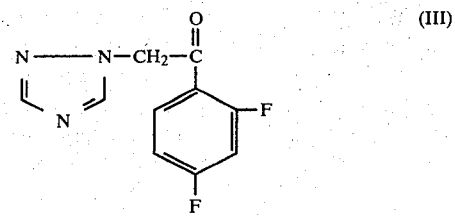

with dimethyloxosulfonium methylide, which is, in turn, prepared from trimethylsulfoxonium iodide and cetyltrimethylammonium bromide (cetrimide) in the presence of aqueous sodium hydroxide.

In practice, this particular reaction is conducted by heating the ketone of formula (III) with trimethylsulfoxonium iodide and cetrimide in a mixture of toluene and aqueous sodium hydride, with vigorous agitation, for a period of a few hours up to a temperature of about 100° C. The oxirane product (II) can then be isolated by conventional procedures.

The ketone starting material of formula (III) is easily prepared by conventional means and preferably by reacting 2-chloro-2',4'-difluoroacetophenone with 1,2,4-triazole in the presence of a base. 2-Chloro-2',4'-difluoroacetophenone is a known compound.

In addition, the invention provides still another method (2) for preparing the compound of the formula (I), viz., one which involves a process starting from the corresponding 1,3-bishalo-2-(2,4-difluorophenyl)propan-2-ol of the formula:

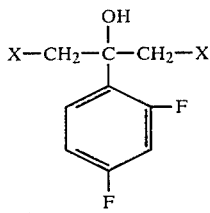

(IV)

wherein X is either chlorine or bromine, whereby said formula (IV) compound is treated with a base in accordance with the procedure described in the *Journal of Organic Chemistry*, Vol. 27, p. 2241 (1962) of form the corresponding oxirane of the formula:

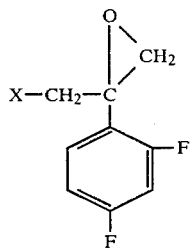

(V)

followed by reaction of said oxirane compound of formula (V) with 1,2,4-triazole in the presence of a base to yield the desired final product (I). The intermediate oxirane compound of the formula (V) can be isolated if so desired.

In a typical reaction procedure, the compound of the formula (IV) and 1,2,4-triazole are heated together in a suitable organic solvent, such as dry dimethylformamide or tetrahydrofuran, to a temperature of up to about 120° C. for a period of up to about 24 hours and preferably, in the presence of an inorganic base such as potassium carbonate, for example. The bis-triazole final product (I) can then be isolated and purified by conventional means.

The bis-halo starting material of formula (IV) can also be obtained by conventional means and preferably, by treating the commercially available 1,3-dichloroacetone with an organometallic reagent of the formula:

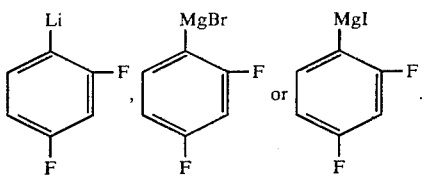

In both the overall methods (1) or (2) for preparing the compound of the formula (I) according to the invention, the desired bis-triazole final product (I) will generally be contaminated with the isomer in which one of the triazole rings is attached to the adjacent methylene moiety via the 4-position of the heterocyclic ring. However, this unwanted isomeric side product can easily be removed from the mixture by means of chromatography on silica gel, for example, or else by recrystallization from a suitable solvent, such as isopropanol, for the present purposes at hand.

As previously indicated, the pharmaceutically acceptable salts of this invention are preferably the acid addition salts. Pharmaceutically acceptable acid addition salts of the compound of formula (I) are those salts formed from strong acids which yield non-toxic acid addition salts containing pharmaceutically acceptable anions, such as the hydrochloride, hydrobromide and sulfate salts, etc. These salts may be obtained by employing conventional procedures such as, for example, by mixing solutions containing equimolar amounts of the free base (I) and the desired acid together, followed by filtration to collect the required salt, if insoluble, or else by evaporation of the solvent from the system in accordance with standard techniques.

The compound of the formula (I) and its pharmaceutically acceptable acid addition salts are very active antifungal agents and are therefore useful in combatting fungal infections in animals, including humans. For example, they are useful in treating topical fungal infections in man caused by, among other organisms, various species of Candida, Trichophyton, Microsporum or Epidermophyton. They are also useful in treating various mucosal infections in man caused by *Candida albicans*, such as, for example, thrush and vaginal candidiasis. In addition, they may also be used in the treatment of systemic fungal infections caused by such as organisms as *Candida albicans, Cryptococcus neoformans, Aspergillus fumigatus*, Coccidioides, Paracoccidioides, Histoplasma or Blastomyces, for example.

The in vitro evaluation of the antifungal activity of the compound of formula (I) can be performed by determining the minimum inhibitory concentration (m.i.c.), which is the concentration of the test compound in a suitable medium at which growth of the particular micro-organism fails to occur. In practice, a series of agar plates, each having the test compound incorporated therein at a particular concentration level, are routinely inoculated with a standard culture of, for example, *Candida albicans* and each plate is then incubated for a period of 48 hours at 37° C. The plates are thereafter examined for the presence or absence of growth of the fungus and the appropriate m.i.c. value is noted. Other micro-organisms employed in such tests can include species like *Cryptococcus neoformans, Aspergillus fumigatus*, Trichophyton spp, Microsporum spp, *Epidermophyton floccosum, Coccidioides immitis* and *Torulopsis glabrata*.

The in vivo evaluation of the compound of formula (I) can be carried out at a series of different dose levels by intravenous (i.v.) or interperitoneal (i.p.) injections or by oral administration (p.o.) to mice, which are inoculated with a strain of *Candida albicans*. The untreated mice die within a period of 48 hours and the dose level at which the compound provides 50% protection against the lethal effect of the infection is duly noted. In this particular case, the compound of formula (I) gives at least 50% protection at a level below 0.5 mg./kg. (p.o. or i.v.).

For human use, the antifungal compound of the formula (I), or a pharmaceutically acceptable acid addition salt thereof, can be administered alone, but will generally be administered in admixture with a pharmaceutical carrier selected with regard to the intended route of administration and standard pharmaceutical practice. For instance, it may be administered orally in the form of a tablet containing such excipients as starch or lactose, or in a capsule or ovule either alone or in admixture with excipients, or in the form of an elixir or suspension containing a flavoring or coloring agent. It may also be injected parenterally, for example, intramuscularly, intravenously or subcutaneously. For purposes of parenteral administration, it is best used in the form of a sterile aqueous solution which may contain other solutes like, for example, sufficient saline or glucose to make the solution isotonic.

For oral and parenteral administration to human patients, the daily dosage level of the antifungal compound of the formula (I) will be from about 0.1 to 5.0 mg./kg. per day, in divided doses, when administered by either the oral or parenteral route. Thus, tablets or capsules can generally be expected to contain anywhere from approximately 5.0 to 500 mg of the active compound for administration singly or two or more at a time as deemed appropriate. The physician will, in any event, determine the actual dosage to be employed for the present purposes at hand and this will be the dosage which is most suitable for an individual patient and will vary accordingly with the age, weight and response of the particular subject. The above dosages are merely exemplary of the average host. There can, of course, be individual instances where higher or lower dosage ranges are clearly merited and such dosages are understood to be within the scope of this invention.

Alternatively, the antifungal compound of the formula (I) may be administered in the form of a suppository or pessary, or it may be applied topically in the form of a lotion, solution, ointment or paste, or as a dusting powder. For example, it may be incorporated into an ointment consisting of an aqueous emulsion of polyethylene glycols or liquid paraffin; or it may be incorporated, at a concentration level between 1 and 10%, into an ointment consisting of a white wax or a white soft paraffin base, together with such stabilizers and preservatives as may be required.

PREPARATION A

To a stirred mixture consisting of 114 g. (1.0 mole) of 1,3-difluorobenzene and 146.6 g. (1.1 mole) of aluminum chloride at room temperature (20° C.), there were added in a dropwise manner 113 g. (1.0 mole) of chloroacetyl chloride also at room temperature. The reaction mixture was then stirred for a further period of five hours while at 50°–55° C. Upon completion of this step, 48.5 ml. of methylene chloride was slowly added to the spent mixture as the latter was allowed to cool to room temperature. The methylene chloride layer was then separated, washed twice with 320 ml. of water and finally evaporated under reduced pressure to afford 180 g. of a pale yellow solid. A 145 g. portion of the crude material was then crystallized from n-hexane (435 ml.) to give 113 g. (73%) of pure 2-chloro-2',4'-difluoroacetophenone, m.p. 47°–49° C. [literature m.p. 46.5° C., according to Von D. Ehlers et al., *J. Prakt. Chem.*, Vol. 315, p. 1169 (1973)]. The pure product was further characterized by means of infrared absorption spectra and nuclear magnetic resonance data.

PREPARATION B

To a mixture consisting of 30.4 g. (0.44 mole) of 1,2,4-triazole and 15.1 g. (0.15 mole) of triethylamine in 186 ml. of refluxing ethyl acetate, there was added a solution of 38.1 g. (0.20 mole) of 2-chloro-2',4'-difluoroacetophenone (prepared as described in Preparation A) in 80 ml. of ethyl acetate. The resulting reaction mixture was then refluxed for a period of six hours and finally cooled to room temperature. At this point, the insolubles were removed by means of filtration and the filtrate was washed with two-200 ml. portions of water. After removal of the solvent from the washed filtrate by means of evaporation under reduced pressure, the crude product was dissolved in 150 ml. of fresh ethyl acetate and treated with 25% w./v. hydrogen chloride gas in isopropanol. The resulting mixture was then granulated at 0° C. for a period of one hour and the crystalline salt was subsequently collected by means of suction filtration and air dried to constant weight to afford 21.6 g. (40%) of pure 2',4'-difluoro-2-(1H-1,2,4-triazol-1-yl)acetophenone hydrochloride, m.p. 167°–170° C. The pure product was further characterized by means of infrared absorption spectra and nuclear magnetic resonance data.

PREPARATION C

To a stirred slurry consisting of 16.8 g. (0.20 mole) of sodium bicarbonate and 27.6 g. (0.40 mole) of 1,2,4-triazole in 180 ml. of refluxing toluene, there was added a solution consisting of 38.1 g. (0.20 mole) of 2-chloro-2',4'-difluoroacetophenone (prepared as described in Preparation A) dissolved in 45 ml. of toluene. The resulting mixture was then stirred at reflux for a period of three hours and the water formed during the course of the reaction was removed by using a Dean and Stark trap in a conventional manner. Upon completion of this step, the spent reaction mixture was cooled to room temperature and 180 ml. of water was added to the mixture. At this point, the toluene layer was separated and the solvent subsequently removed therefrom by means of distillation at reduced pressure. The residual solid material, which consisted of a pale brown solid, was crystallized from 70 ml. of ethyl acetate/n-hexane (1:1 by volume) to ultimately afford 3.9 g. (87%) of pure 2',4'-difluoro-2-(1H-1,2,4-triazol-1-yl)acetophenone, m.p. 103°–105° C. The pure product was further characterized by means of infrared absorption spectra and nuclear magnetic resonance data, in addition to elemental analysis.

Anal. Calcd. for $C_{10}H_7F_2N_3O$: C, 53.80; H, 3.16; N, 18.82 Found: C, 53.62; H, 3.15; N, 18.68.

PREPARATION D

A mixture consisting of 59.6 g. (0.23 mole) of 2',4'-difluoro-2-(1H-1,2,4-triazol-1-yl)acetophenone (prepared as described in Preparation C), 50.6 g. (0.23 mole)

of trimethylsulfoxonium iodide and 2.1 g. of cetyltrimethylammonium bromide was stirred in 370 ml. of toluene together with 20% w./w. of aqueous sodium hydroxide at 60° C. for a period of three hours. The toluene layer was then separated and concentrated in vacuo to a volume of 110 ml., followed by dilution with 150 ml. of ethyl acetate. A solution of 16.6 g. (0.172 mole) of methanesulfonic acid dissolved in 20 ml. of ethyl acetate was then added to the diluted organic solution, followed by a further dilution of the resulting mixture with 100 ml. of ethyl acetate. At this point, the final mixture was stirred at 0° C. for a period of one hour and then filtered to afford 43 g. (56%) of crude 1-[2-(2,4-difluorophenyl)-2,3-epoxypropyl]-1H-1,2,4-triazole methanesulfonate as the recovered precipitate.

A 20 g. portion of the crude material was then dissolved in 140 ml. of hot industrial methylated spirits (i.e., ethyl alcohol denatured with methanol) and 2.0 g. of activated carbon were added. The mixture was then filtered and the filtrate subsequently concentrated in vacuo to 100 ml., prior to stirring same at 0° C. for a period of one hour. Filtration of the latter cooled concentrate then gave 7.8 g. (39%) of pure 1-[2-(2,4-difluorophenyl)-2,3-epoxypropyl]-1H-1,2,4-triazole methanesulfonate, m.p. 128°-129° C. The pure product was further characterized by means of infrared absorption spectra and nuclear magnetic resonance data, in addition to elemental analysis.

Anal. Calcd. for $C_{12}H_{13}F_2N_3O_4S$: C, 43.24; H, 3.94; N, 12.61. Found: C, 42.83; H, 3.92; N, 12.96.

EXAMPLE 1

A solution consisting of 960 mg. (0.005 mole) of 1-bromo-2,4-difluorobenzene dissolved in 10 ml. of diethyl ether was stirred at −78° C., while 3.23 ml. of 1.55 M n-butyl lithium (0.005 mole) in n-hexane was slowly added thereto over a period of three minutes. After the addition was complete, the mixture was stirred for a further period of ten minutes and then a solution consisting of 630 mg. (0.005 mole) of 1,3-dichloroacetone dissolved in 10 ml. of diethyl ether was added dropwise to the stirred ethereal mixture over a period of three minutes. After the latter addition was complete, the reaction mixture was stirred for a further period of 30 minutes at −78° C., while a solution consisting of 330 mg. of glacial acetic acid dissolved in 5 ml. of diethyl ether was slowly added thereto at 0° C., followed by the addition of 10 ml. of water. Upon completion of this step, the organic layer was separated and the aqueous phase was extracted once with fresh diethyl ether. The combined ethereal extracts were then dried over anhydrous magnesium sulfate and filtered, and the resulting filtrate was subsequently evaporated under reduced pressure to afford a pale yellow oil as the residual liquid. The latter material, which consisted essentially of pure 1,3-bischloro-2-(2,4-difluorophenyl)propane-2-ol, was dissolved in 20 ml. of dimethylformamide and used as such in the next reaction step.

To the solution prepared above, 1.72 g. (0.025 mole) of 1,2,4-triazole and 2.07 g. (0.015 mole) of anhydrous potassium carbonate were added and the resulting mixture was heated at 70° C. for a period of 18 hours. The reaction mixture thus obtained was then poured into 100 ml. of water and the resulting aqueous mixture was extracted twice with ethyl acetate. The combined organic extracts were then dried over anhydrous magnesium sulfate and filtered, and the resulting filtrate was subsequently evaporated under reduced pressure to give a gum. The latter material was then chromatographed on silica (270-400 mesh), using 3% methanol in methylene chloride as the eluant, to ultimately afford 400 mg. (26%) of pure 2-(2,4-difluorophenyl)-1,3-bis(1H-1,2,4-triazol-1-yl)propan-2-ol in the form of a white solid, m.p. 138°-140° C. after recrystallization from ethyl acetate/n-hexane. The pure product was further characterized by means of mass spectroscopy, nuclear magnetic resonance data and infrared absorption spectra, in addition to elemental analysis.

Alal. Calcd. for $C_{13}H_{12}F_2N_6O$: C, 50.98; H, 3.95; N, 27.44. Found: C, 51.33; H, 4.05; N, 27.08.

EXAMPLE 2

A mixture consisting of 6.7 g. (0.02 mole) of 1-[2-(2,4-difluorophenyl)-2,3-epoxypropyl]-1H-1,2,4-triazole methanesulfonate (prepared as described in Preparation D), 2.8 g. (0.04 mole) of 1,2,4-triazole and 0.1 g. (0.066 mole) of anhydrous potassium carbonate was stirred in 35 ml. of dimethylformamide at 90° C. for a period of 4.5 hours. The resulting mixture was then cooled to room temperature and added to 170 ml. of water. The aqueous mixture so obtained was next extracted with two-60 ml. portions of chloroform, and the resulting organic extracts were thereafter combined and subsequently washed with two-100 ml. portions of water. After drying the washed organic solution over anhydrous magnesium sulfate (and filtering), the solvent was removed from the filtrate by means of evaporation under reduced pressure to afford 5.3 g. of crude product as the residue.

The crude product (5.3 g.) was then dissolved in 50 ml. of isopropanol and 0.5 g. of activated carbon was added to the aforesaid solution. The resulting mixture was then filtered and the filtrate concentrated in vacuo to 25 ml. to ultimately afford a precipitate. The latter material was subsequently collected by means of suction filtration and air dried to constant weight to give 2.64 g. (44%) of pure 2-(2,4-difluorophenyl)-1,3-bis(1H-1,2,4-triazol-1-yl)propan-2-ol, m.p. 139°-140° C. The pure product was further characterized by means of infrared absorption spectra and nuclear magnetic resonance data, in addition to elemental analysis.

Anal. Calcd. for $C_{13}H_{12}F_2N_6O$: C, 50.98; H, 3.92; N, 27.44. Found: C, 50.85; H, 3.92; N, 27.74.

I claim:

1. An antifungal compound selected from the group consisting of 2-(2,4-difluorophenyl)-1,3-bis(1H-1,2,4-triazol-1-yl)propan-2-ol and the pharmaceutically acceptable acid addition salts thereof.

2. A pharmaceutical composition comprising a pharmaceutically acceptable carrier and an effective antifungal amount of a compound as claimed in claim 1.

3. A method for treating fungal infections in a warm-blooded animal, which comprises administering to said animal an effective antifungal amount of a compound as claimed in claim 1.

* * * * *

UNITED STATES PATENT AND TRADEMARK OFFICE

CERTIFICATE EXTENDING PATENT TERM
UNDER 35 U.S.C. 156

Patent No.    : 4,404,216

Dated         : September 13, 1983

Inventor(s)   : Kenneth Richardson

Patent Owner  : Pfizer, Inc.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of 1,128 DAYS with all rights pertaining thereto as provided by 35 U.S.C. 156 (b).

I have caused the seal of the Patent and Trademark Office to be affixed this 25th day of July, 1991.

Harry F. Manbeck, Jr.
Assistant Secretary and Commissioner of Patents and Trademarks